United States Patent
Viebach et al.

(10) Patent No.: US 6,899,674 B2
(45) Date of Patent: May 31, 2005

(54) ENDOSCOPE SHAFT COMPRISING A MOVABLE END PORTION

(75) Inventors: Thomas Viebach, Pischertshofen (DE); Fritz Pauker, Friedberg (DE)

(73) Assignee: STM Medizintechnik Starnberg GmbH, Weinheim (DE)

( * ) Notice: Subject to any disclaimer, the term of this patent is extended or adjusted under 35 U.S.C. 154(b) by 21 days.

(21) Appl. No.: 10/368,734

(22) Filed: Feb. 19, 2003

(65) Prior Publication Data

US 2003/0181785 A1 Sep. 25, 2003

(30) Foreign Application Priority Data

Mar. 7, 2002 (DE) .......................................... 102 09 986

(51) Int. Cl.⁷ ................................................ A61B 1/00
(52) U.S. Cl. ....................... 600/152; 600/115; 600/116; 600/139; 600/143; 600/146
(58) Field of Search .................................. 600/115, 116, 600/143, 146, 152, 139

(56) References Cited

U.S. PATENT DOCUMENTS

| | | | |
|---|---|---|---|
| 4,890,602 A | * | 1/1990 | Hake .......................... 600/144 |
| 5,577,992 A | | 11/1996 | Chiba et al. |
| 5,860,914 A | * | 1/1999 | Chiba et al. ................. 600/151 |
| 6,503,194 B2 | | 1/2003 | Pauker |

FOREIGN PATENT DOCUMENTS

| | | |
|---|---|---|
| DE | 44 35 644 A1 | 4/1995 |
| DE | 100 10 932 A1 | 9/2001 |
| WO | WO 01/80935 A1 | 11/2001 |

* cited by examiner

*Primary Examiner*—Beverly M. Flanagan
*Assistant Examiner*—Matthew Kasztejna
(74) *Attorney, Agent, or Firm*—Mayer, Brown, Rowe & Maw LLP; David M. Thimmig

(57) ABSTRACT

The present invention relates to an endoscope shaft comprising a movable distal end portion which is bendable by means of an operating device, the distal end portion having at least one decentralized hose member extending along the distal end portion, said hose member being integrally formed of a plurality of directly superimposed expansion bellows and forming a continuous pressure chamber so as to expand in the longitudinal direction when pressure is applied.

26 Claims, 5 Drawing Sheets

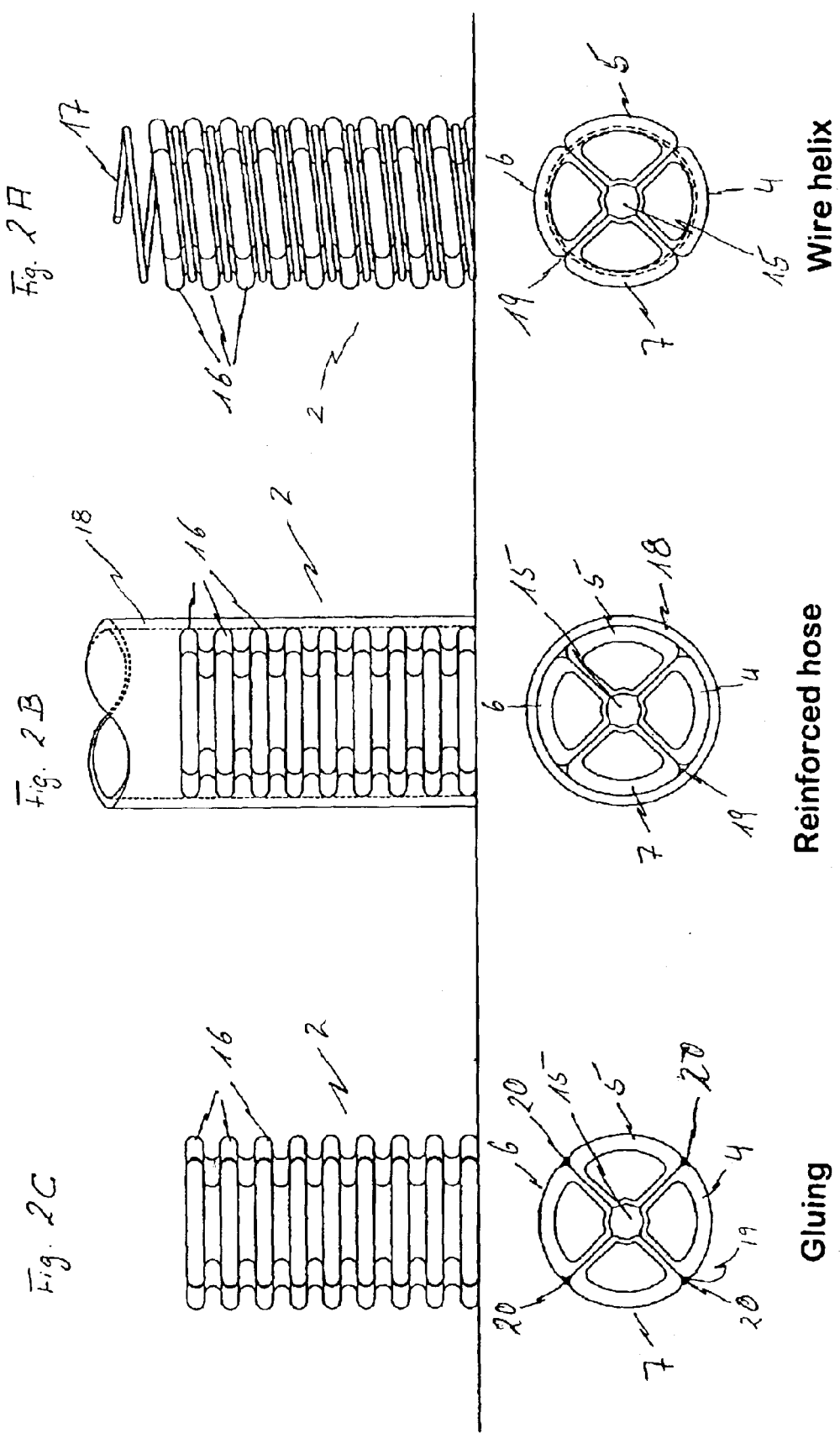

$P_0 = 0$  $P_1 > P_0$  $P_2 > P_1$

Pressure behavior of a chain of segments

ENDOSCOPE SHAFT COMPRISING A MOVABLE END PORTION

BACKGROUND OF THE INVENTION

The present invention relates to an endoscope shaft having a movable distal end portion which is bendable by means of an operating device, and in particular to an endoscope shaft having a plurality of hose members disposed in a decentralized manner.

Endoscopes are instruments especially for exploring hollows or tube-shaped conduits of the body, especially for medical purposes. In particular endoscopes for exploring the esophagus, the stomach, the duodenum from the stomach, the intestine from the anus, the urethra, the vesica and the ureter have become known. Such an endoscope is equipped with a lighting device at its front end and with an optical system for visually detecting the area located in front of the body hollow or body canal to be explored. While until recently the optical information detected ahead of the front end of the endoscope was usually transmitted by means of fiber optics through the endoscope towards its operating portion behind, the insertion of a camera chip at the front endoscope tip as well as the electric image transmission and the illustration of the optical information obtained on a video monitor constitutes the latest prior art now.

Furthermore, endoscopes usually comprise a so-called working conduit through which various working instruments can be introduced and operated. For example, small forceps for taking tissue specimens, biopsy needles, heated cutting wires, small scissors, coagulation electrodes or the like are introduced so as to perform surgical measures at the affected tissue, if need be. Finally, as a rule, a fluid conduit for wash and operating wires for bending the front end of the endoscope in various directions are provided. These operating wires are guided through individual conduits within the endoscope shaft towards the front or distal end thereof, respectively, so as to bend it three-dimensionally by up to 160° in the opposite direction of the endoscope shaft.

In this connection, essential problems arise now, especially with respect to the tactile feeling which is given to the operator during the bending process of the distal end. Therefore, there is the risk that, when the intestine is explored, the intestine wall is injured during the bending process of the distal end. Furthermore, it must be possible to be able to exactly position the distal end in the area to be explored and to be treated, if necessary, which requires a sufficient flexibility as well as at the same time a sufficient stiffness, after the predetermined bending position has been reached.

To solve this problem a prior art device according to DE 100 10 932 A1 is provided to form the distal end portion of a plurality of bellow-shaped disc bodies and/or swelling bodies which are longitudinally juxtaposed and/or stacked, two of which at a time are located diametrically with respect to each other and form a body layer and two longitudinally directly adjacent pairs of bodies of which are phase-shifted by 90°. Thereby, a construction is obtained in which the individual disc-like swelling bodies, seen in the longitudinal direction, are alternately arranged at twelve and six o'clock according to the one layer and at three and nine o'clock according to the neighboring and/or superimposed layer. In this way it is possible to achieve a bend-off of the distal end into the intended direction by correspondingly operating the bellows having the same angular position when they are swelling or contracting, wherein, when the predetermined angular position of the distal end has been reached, the swelling bodies are virtually frozen in this position and thus the position of the distal end is fixed.

Tests have shown in the meantime that the manufacture of a distal end of the aforementioned disc-like swelling bodies is extremely expensive, because they have to be hydraulically interconnected in a fluid-tight manner. The manufacture of the swelling bodies themselves thus is extremely costly and the assembly of the swelling bodies is labor-intense. Therefore the endoscope shaft manufactured in this way is rather unsuited for a throw-away article for reasons of costs.

SUMMARY OF THE INVENTION

In view of the aforementioned problems, it is the object of the invention to provide a construction for a distal end portion of an endoscope shaft which can be manufactured at reasonable costs and nevertheless has an improved functionality.

This object is achieved, according to the invention, by an endoscope shaft comprising the features of claim 1.

Accordingly, the endoscope shaft according to the invention comprises a movable distal end portion which is bendable by means of an operating device. The distal end portion includes at least one hose member arranged to be decentralized with respect to the longitudinal axis of the endoscope shaft and extending along the distal end portion which is integrally formed of a plurality of expansion bellows disposed directly, i.e. superimposed on a straight line and forming a continuous pressure chamber. When pressure is applied to this pressure chamber the hose member expands in its longitudinal direction and thus necessarily causes a bending of the distal end portion by virtue of its decentralized arrangement.

The hose members preferably are disposed such that the folds formed by the bellows define one or a plurality of continuous circumferential grooves by aligning the folds of each bellow to each other on the circumferential surface of the end portion.

The arrangement of the aforedescribed hose-like expansion bellows has the advantage vis-à-vis the prior art cited in the beginning that it can be manufactured in a simple way, for instance by extrusion molding already as one single component and as such it need no longer be assembled and welded when it is mounted in the distal end portion.

By virtue of the longitudinal extension of the hose-like expansion bellow member, possibly not only a longitudinal expansion but also a more or less large widening in the radial direction which could possibly result in a radial extension of the entire distal end portion may occur when pressure is applied. In order to safely avoid this, it is provided as an advantageous further development of the subject matter of the invention to arrange a means for reducing a swelling of the respective hose member transversely to the longitudinal direction thereof. Preferably, the means for reducing a swelling is a supporting corset disposed at one outside of the hose member. The advantage of this embodiment consists in the fact that the arrangement of the outer supporting corset can be taken as an optional measure depending on the pressure ratios to be expected as well as on the existing mounting space and also differently dimensioned corsets can be employed. This permits the design of a quasi uniform hose member which can then be adapted to the individual applications. Thus the overall manufacturing costs are further reduced.

Further advantageous configurations of the invention are the subject matter of the subclaims.

BRIEF DESCRIPTION OF THE DRAWINGS

Hereinafter the invention is illustrated in detail by way of preferred embodiments with reference to the accompanying drawings.

FIG. 2A shows the movable distal end according to FIG. 1 in an enlarged illustration.

FIG. 2B shows a movable distal end in accordance with a second preferred embodiment of the invention.

FIG. 2C shows a movable distal end in accordance with a third preferred embodiment of the invention.

DETAILED DESCRIPTION OF THE PREFERRED EMBODIMENTS

Figure 1:
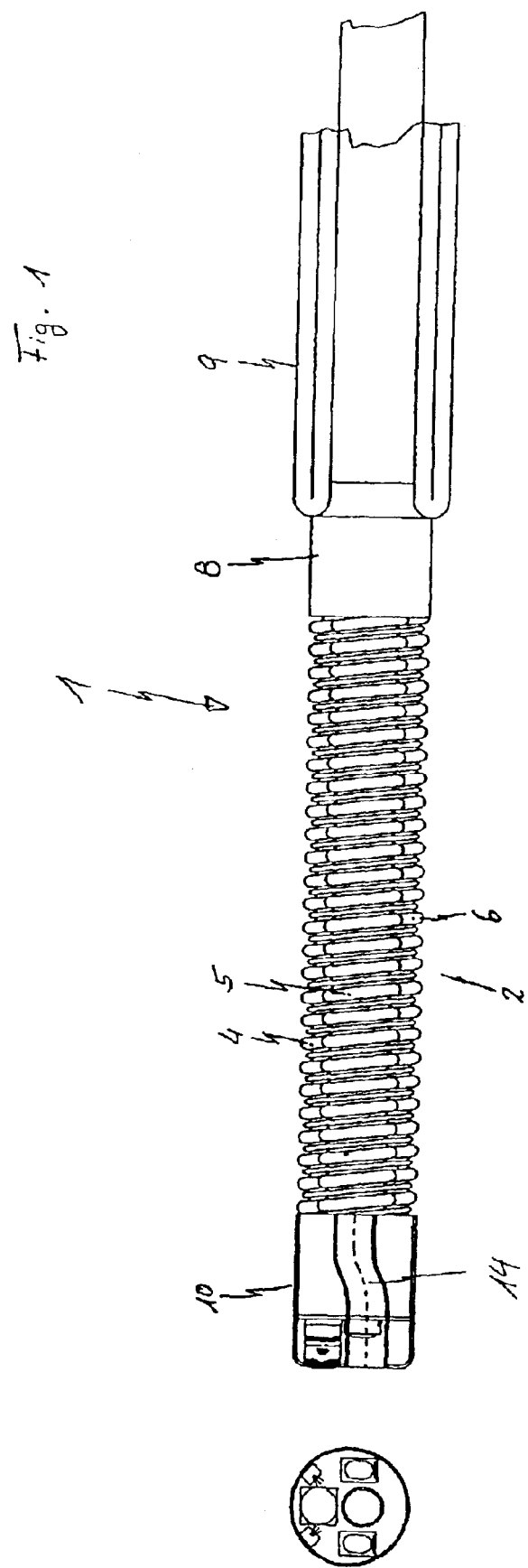
FIG. 1 shows the front portion of an endoscope shaft including its movable distal end in accordance with a first preferred embodiment of the invention.

As one can take especially from FIG. 1, the endoscope shaft 1 in accordance with the first preferred embodiment of the invention has a movable distal end portion 2 adapted to be bent by means of an operating device 3 as it will be described hereinafter by way of FIG. 5 as a possible embodiment which can also be designed differently, however. The distal end portion 2 includes at least one (four in the present case) decentralized hose member 4–7 extending along the distal end portion which is integrally formed of a plurality of (at least two) extension bellows substantially superimposed on a straight line so as to achieve this longitudinal extension. This hose-like elongated expansion bellow member forms a single, i.e. integrated pressure chamber in such a manner that the expansion bellow member substantially extends in the longitudinal direction only, whereby the movable end portion bends due to the decentralized arrangement of the at least one expansion bellow member.

The endoscope shaft 1 moreover includes a rear shaft portion 8 to the rear end of which (not shown in FIG. 1) the operating device 3 for the distal end portion 2 is connected and which is preferably used in a feed means 9 comprising a reversing hose system known from prior art. The rear shaft portion 8 includes a number of working, supply and operating conduits separated from each other through which for instance hydraulic fluid for individually applying pressure to the hose members 4–7, cleansing liquids, working instruments or simply cables for optical or electric means can be guided at a shaft head 10 arranged at the distal end of the end portion 2.

The movable distal end portion 2 is fixedly connected to the front end of the rear shaft portion 8 in such a manner that the conduits formed in the rear shaft portion 8 open into corresponding conduits inside the distal end portion 2 in a fluid-tight manner. Preferably the distal end portion 2 here-for is non-detachably welded to the rear shaft portion 8, wherein also a detachable plug-in or screw-in connection is possible, of course.

Figure 3A:
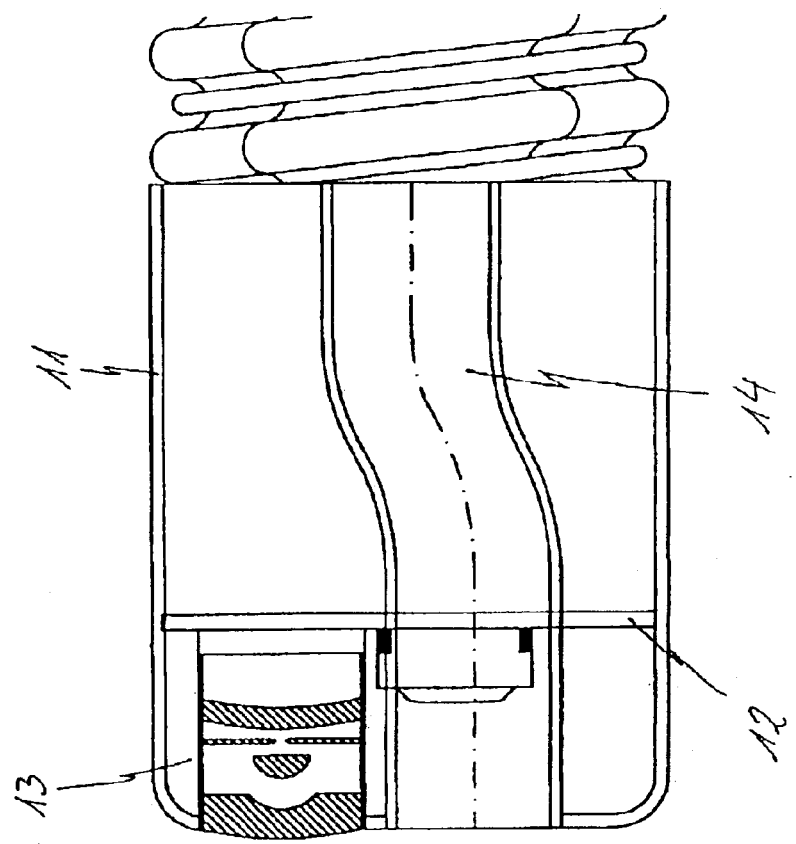
FIG. 3A shows a shaft head in a top view including the movable end portion according to the first preferred embodiment, wherein the shaft head can also be placed upon the movable end portion according to the second or third embodiment.
Figure 3B:
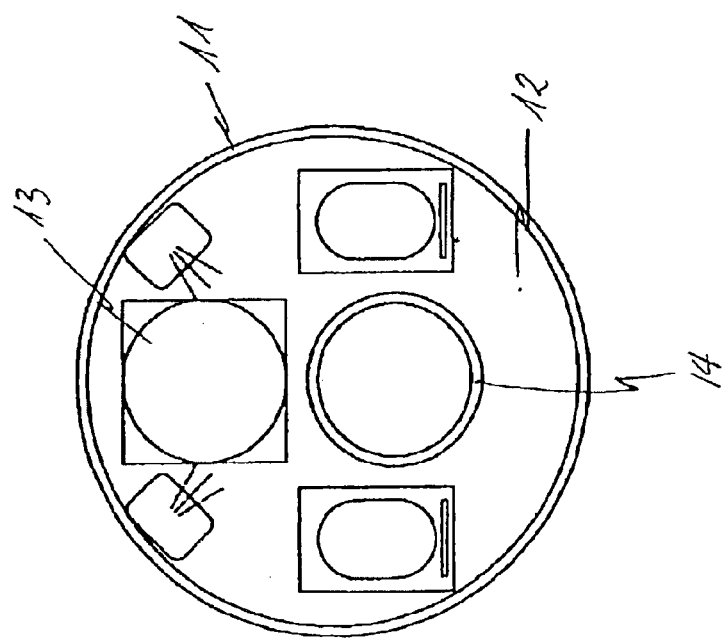
FIG. 3B shows a shaft head in a side view including the movable end portion according to the first preferred embodiment, wherein the shaft head can also be placed upon the movable end portion according to the second or third embodiment.
Figure 4A:
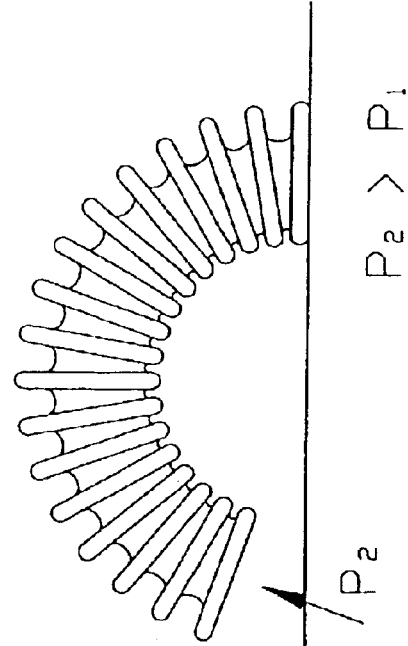
FIGS. 4A to 4C show the motion behavior of the distal end according to the invention when pressure is applied.
Figure 4B:
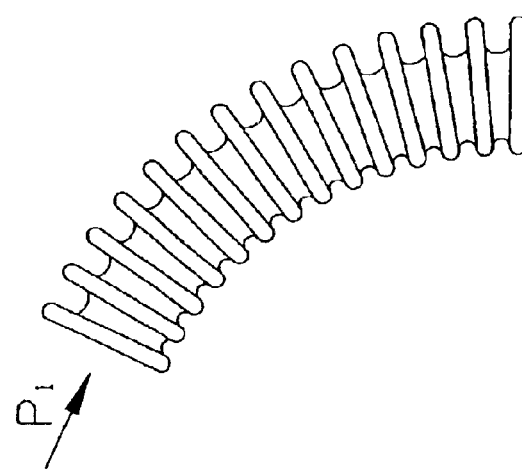
Figure 4C:
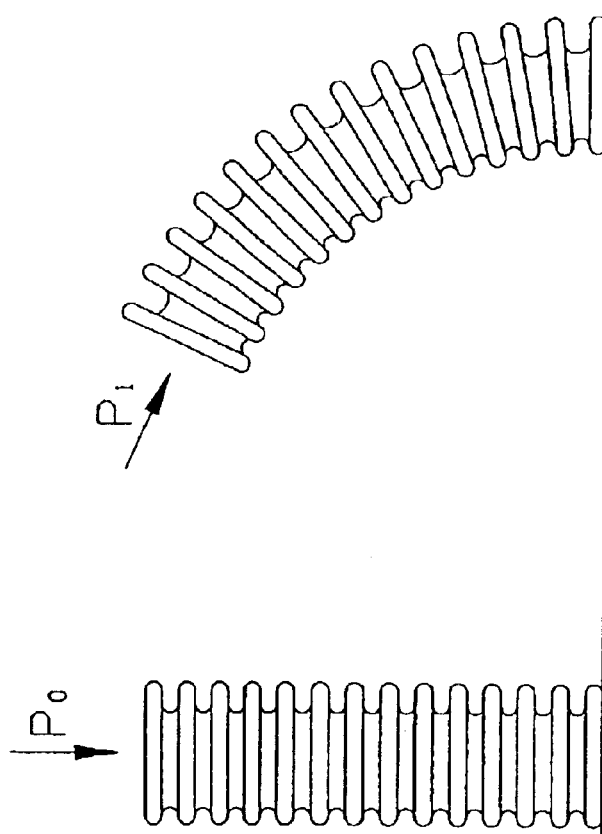

The shaft head 10 is connected to the front end of the distal end portion 2, especially in the same way as the distal end portion 2 is to the rear shaft portion 8. As it is indicated in FIG. 1 and represented enlarged in FIGS. 3A and 3B, the shaft head 10 consists of a housing 11 closed at least at the front face in which a board 12 aligned at a parallel distance from the housing face is inserted. On the board 12 a photocell or a camera chip 13 as well as lighting bodies are mounted which sealingly project through corresponding openings at the housing front. Moreover a central working conduit 14 which is likewise guided through the board 12 and opens into an aperture at the housing front is laid in the housing 11. As one can take from the top view according to FIG. 3B, on both sides of the working conduit 14 further supply conduits, for instance for supplying cleansing liquid or air, are provided.

In FIG. 2A to 2C different embodiments of the distal bendable end portion 2 are illustrated both in a lateral view and in cross-sectional view.

Accordingly, the movable distal end portion 2 according to FIG. 2A comprises four hose members 4, 5, 6, 7, each of which has the shape of a quarter circle in cross-section. Each hose member 4–7 consists of a hose-like hollow of an as non-extensible as possible but flexible material, such as a reinforced synthetic material the wall thickness of which is greater in the outer partial circle portion than at the two straight flank portions. Moreover each hose member 4–7 is formed in the cross-sectional view as an internal partial circle which, when all four hose members 4–7 are assembled, encloses a central inner conduit 15 connected to the corresponding working conduit 14 in the shaft head 10 and to the working conduit in the rear shaft portion 8.

In the side view according to FIG. 2A the folding structure of each hose member 4–7 is apparent. Accordingly, each hose member 4–7 has a plurality of radially projecting protuberances which are arranged obliquely with respect to the longitudinal axis of the hose member 4–7. After assembling all four hose members 4–7, herefrom an outer closed helical shape is resulting by the protuberances 16.

Further the distal end portion 2 is enclosed by a kind of outer supporting corset which is intended to prevent the respective hose member 4–7 from radially swelling when pressure is applied. In the present embodiment according to FIG. 2A, this outer supporting corset is formed of a helical spring 17 the gradient and dimension of which is adapted to the outer helical shape of the distal end portion 2 and which is inserted between the radially projecting protuberances 16, i.e. into the valleys of the helical shape. The helical spring wire is preferably designed such (for instance so as to be rectangular or oval) that it permits an as unforced bending of the spring 17 as possible, but develops a high resistance to a radial expansion of the spring 17. The spring 17 furthermore exerts an inwardly directed radial force on the hose members 4–7 to keep them in their relative position.

In FIG. 2B a second preferred embodiment is shown for the movable distal end portion 2 according to the invention, wherein identical reference numerals are used for parts which are equal to the first embodiment.

In this second embodiment the supporting corset is made of an elastic hose-like envelope 18 which is pulled over the assembled hose members 4–7 under a predetermined prestress so as to hereby exert a radially inwardly directed force on the hose members 4–7. In order to obtain an even faster connection between the envelope 18 and the hose members 4–7, the envelope 18 may be shrunk onto the hose members 4–7 or glued to the same. As one can further take from FIG. 2B, the expansion bellow structure of each hose segment 4–7 according to the second embodiment is different from that of the first embodiment. Since the helical spring 17 is replaced by the hose envelope 18, a helical expansion bellow structure according to FIG. 2A is possible in this case, to be sure, but it is not necessary. Rather, the radially outwardly directed protuberances 16 of each hose member 4–7 are formed as radial ring segments spaced apart in parallel which are completed in the assembled state of the four hose members 4–7 to form circumferential closed rings. In addition to or instead of the elastic envelope 18 individual metallic or synthetic collars (not shown in detail) may be inserted in the valleys between the protuberances 16 which contribute to preventing the hose members 4–7 from radially widening when pressure is applied.

Finally in FIG. 2C a third preferred embodiment for a distal end portion according to the invention is illustrated, wherein also in this case identical reference numerals are used for components already described before.

In this case the hose members 4–7 are designed as in the second embodiment, they may also be designed, however, as in the first embodiment, i.e. having helical protuberances 16. In the assembled state, as in the second embodiment shown in FIG. 2B, longitudinally extending continuous notches 19 are formed at the hose elements 4–7 in the form of quarter circle segments as a result of rounded edges due to manufacture. These notches 19 can be utilized as recess of a supporting corset according to the invention. In the present case the longitudinally extending notches 19 are filled with a glue 20, the notches on the one hand causing, after binding the glue, an outside gluing of the adjacent hose members 4–7 and, on the other hand, serving as reinforcing ropes. This form of a supporting corset can already be realized upon assembling the hose segments 4–7 without the dimensions of the distal end portion 2 enlarging in the radial direction. In so far, these gluings are not only suited as a sole measure for reducing radial widenings due to the application of pressure but especially as a supplementation of the technical measure as described already by way of FIGS. 2A and 2B.

Figure 5:
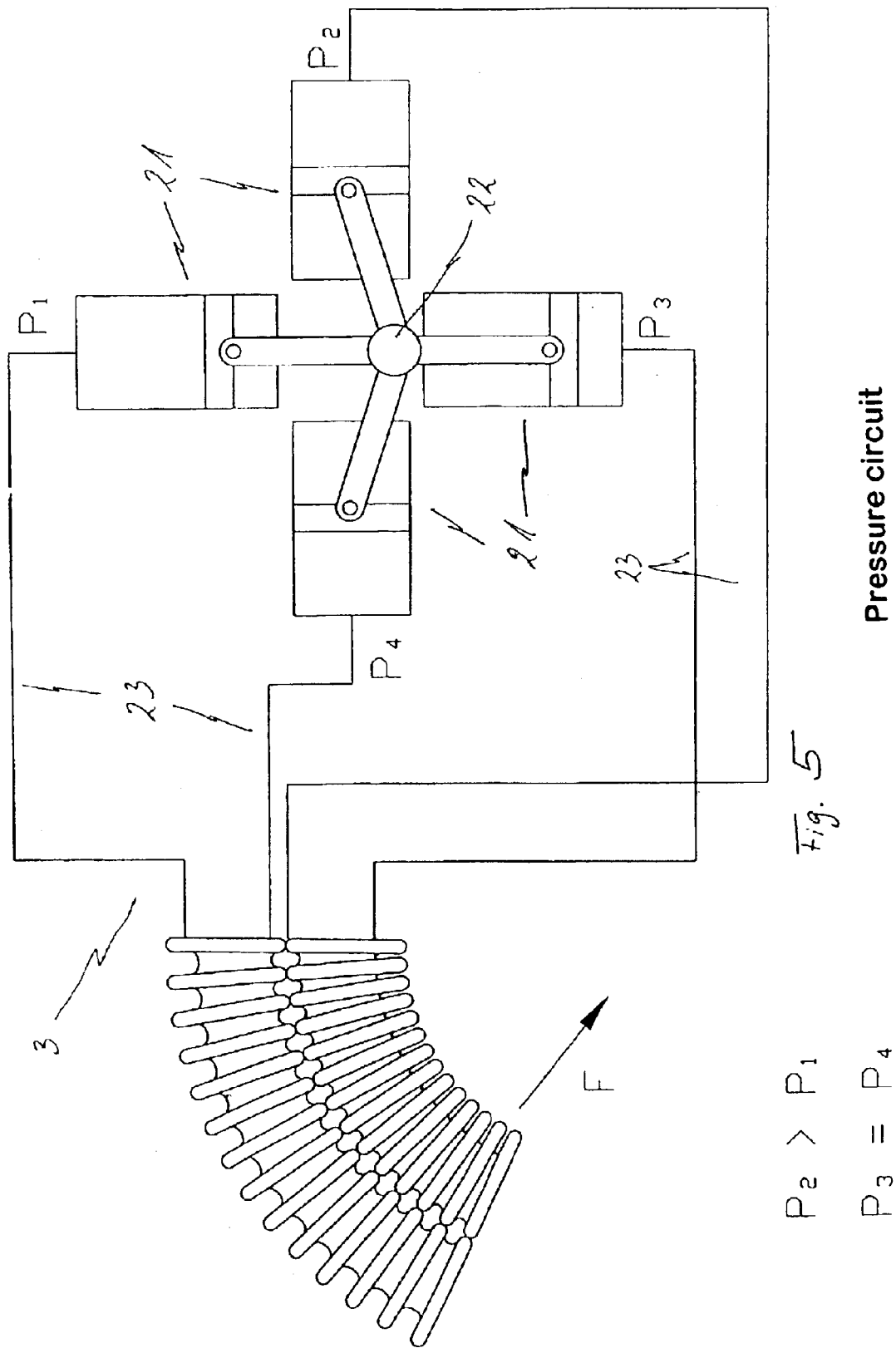
FIG. 5 shows an operating device of the distal end according to the invention.

In FIG. 5, the operating means 3 for the hose members 4–7 of the distal end portion 2 is represented by way of example. Accordingly, it comprises four piston/cylinder or, as an alternative, two double piston/cylinder arrangements 21 which are connected to each other by operating rods 22. Each cylinder, or in the case of the (double-lift) doublethrust double piston cylinders, each cylinder side is hydraulically connected to one of the hose segments 4–7 through the operating conduits inside the endoscope shaft so that upon operation of one cylinder (cylinder side) for applying pressure to a hose member at the same time another cylinder (cylinder side) is operated for appropriately reducing the pressure on the respectively diametrical hose member. In this way at least one hose member is extended in the longitudinal direction while the diametrical hose member is shortened in the longitudinal direction, thereby a bend-off of the distal end portion 2 being effected in the direction of the shortening hose member.

Before the functioning of the endoscope shaft according to the invention especially of the distal end portion 2 is described by way of FIG. 4A to 4C and 5, the following possible modifications of the aforedescribed embodiments are further referred to:

Depending on the intended use and application of the endoscope, it can be manually rotated as a whole inside a hollow to be examined. Hence in this case it is not necessary to design the movable distal end portion to be bendable in all directions. It is rather sufficient to permit a bend-off in one direction only (two-dimensionally). This can be obtained already by only one or two of the decentralized hose members which in this case need not have the shape of a quarter circle but may have any other cross-sectional shape. By this measure not only the constructional effort of the entire endoscope shaft is reduced but also an additional hollow is provided for further or larger operating and supply conduits.

The envelope-shaped hose 18 shown in FIG. 2B can be provided with a reinforcement so that the latter prevents the envelope 18 from radially expanding, but leaves the elasticity of the envelope material in the longitudinal direction largely unaffected.

Although the aforedescribed hose members form a substantially straight, longitudinally extending hollow, it is also possible to impart a helical shape to the hose members so as to cause a kind of progressive circular motion of the shaft head 10 when pressure is applied and a longitudinal extension is substantially resulting herefrom.

All these modifications as well as the above-described embodiments have the design of the hose-like elongated expansion bellow member having one single integral hollow in common, however, which as a single integral component can be easily and cheaply manufactured and assembled in one single manufacturing step. Moreover both the distribution of the wall thicknesses and especially the outer supporting corset serve for preventing a radial expansion, if possible, and for admitting only a longitudinal expansion when pressure is applied.

Concerning the description of the functioning FIG. 4A to 4C and 5 are referred to.

If, consequently, the operating rods 22 are manually shifted, the piston/cylinder units 21 connected thereto are correspondingly operated, whereby hydraulic fluid is guided through hydraulic lines 23 and the hydraulic conduits inside the endoscope shaft 1 to the hose members 4–7 or is discharged from the same. As a pressure is built up hereby in at least one of the hose members 4–7, the same is expanded in the longitudinal direction, whereas the diametrical hose member is shortened in the longitudinal direction by a discharge of the hydraulic fluid. As already indicated before, the outer supporting corset according to the invention prevents or reduces a radial swelling of the hose members 4–7 so that the volume flow of hydraulic fluid is substantially converted only into a longitudinal expansion of the respective hose member. This effect of the outer supporting corset is additionally backed by the fact that the radially outer wall of each hose segment 4–7 is stronger vis-á-vis the flank sides and therefore offers an increased resistance to deformation, i.e. to a radial widening.

By the differences in length of the controlled hose members the distal end portion in which the hose members are anchored is bent off in the direction of the shorter hose member, whereby the shaft head 10 can be moved by up to 180° in each direction. In this way the shaft head 10 can be moved into any position and can there be virtually arrested by fixing the respectively prevailing hydraulic fluid pressures:

We claim:

1. An endoscope shaft comprising a distal cylindrical end portion which is bendable by means of an operating device and which has a plurality of hose members disposed in a decentralized manner and extending along said end portion, each of said hose members forming a continuous pressure chamber so as to extend in a longitudinal direction when pressure is applied, for which purpose each of said hose members forms at least one bellows consisting of a synthetic material non-elastic at least in a predetermined pressure-application range wherein said hose members are disposed such that folds formed by the bellows define continuous circumferential grooves aligned toward each other on a circumferential surface of said end portion, and wherein said circumferential grooves are aligned at an acute angle to a central axis of said end portion such that a helical shape is formed.

2. An endoscope shaft comprising a distal cylindrical end portion which is bendable by means of an operating device and which has a plurality of hose members disposed in a decentralized manner and extending along said end portion, each of said hose members forming a continuous pressure chamber so as to extend in a longitudinal direction when pressure is applied, for which purpose each of said hose members forms at least one bellows consisting of a synthetic material non-elastic at least in a predetermined pressure-application range wherein said hose members are disposed such that folds formed by the bellows define continuous circumferential grooves aligned toward each other on a circumferential surface of said end portion, and wherein each hose member forms, in its cross-section, a segment of a circle with a radial outer side and relatively straight inner sides or flanks and wherein a plurality of said hose members having the shape of a circle segment are adjacent to each other at the flanks.

3. An endoscope shaft according to claim 2, wherein said supporting corset is arranged at a radial outer side jointly formed by said hose members.

4. An endoscope shaft according to claim 2, wherein said supporting corset further comprises a glue bead preferably extending in a longitudinal direction of said hose member and connecting each two directly adjacent hose members.

5. An endoscope shaft according to claim 1, further comprising a means for reducing a swelling of each respective hose member transversely to a longitudinal direction thereof.

6. An endoscope shaft according to claim 5, wherein said means for reducing a swelling further comprises a supporting corset arranged on an outside of said hose member.

7. An endoscope shaft according to claim 6, wherein said supporting corset further comprises a helical spring which is placed into said grooves of said bellows aligned to form a helical shape.

8. An endoscope shaft according to claim 6, wherein said supporting corset further comprises a reinforced hose envelope.

9. An endoscope shaft according to claim 6, wherein said supporting corset further comprises a plurality of collars or rings spaced apart in the longitudinal direction of said endoscope shaft, said collars or rings being placed into said grooves of said bellows aligned towards each other perpendicular to a central axis of said end portion.

10. An endoscope shaft according to claim 1, wherein each hose member forms, in its cross-section, a segment of a circle with a radial outer side and relatively straight inner sides or flanks and wherein a plurality of said hose members having the shape of a circle segment are adjacent to each other at the flanks.

11. An endoscope shaft according to claim 10, wherein said supporting corset is arranged at a radial outer side jointly formed by said hose members.

12. An endoscope shaft according to claim 10, wherein said supporting corset further comprises a glue bead preferably extending in a longitudinal direction of said hose member and connecting each two directly adjacent hose members.

13. An endoscope shaft according to claim 2, wherein said circumferential grooves are aligned perpendicular to a central axis of said end portion.

14. An endoscope shaft according to claim 13, further comprising a means for reducing a swelling of each respective hose member transversely to a longitudinal direction thereof.

15. An endoscope shaft according to claim 14, wherein said means for reducing a swelling further comprises a supporting corset arranged on an outside of said hose member.

16. An endoscope shaft according to claim 15, wherein said supporting corset further comprises a helical spring which is placed into said grooves of said bellows aligned to form a helical shape.

17. An endoscope shaft according to claim 15, wherein said supporting corset further comprises a reinforced hose envelope.

18. An endoscope shaft according to claim 15, wherein said supporting corset further comprises a plurality of collars or rings spaced apart in the longitudinal direction of said endoscope shaft, said collars or rings being placed into said grooves of said bellows aligned towards each other perpendicular to a central axis of said end portion.

19. An endoscope shaft according to claim 13, wherein each hose member forms, in its cross-section, a segment of a circle with a radial outer side and relatively straight inner sides or flanks and wherein a plurality of said hose members having the shape of a circle segment are adjacent to each other at the flanks.

20. An endoscope shaft according to claim 19, wherein said supporting corset is arranged at a radial outer side jointly formed by said hose members.

21. An endoscope shaft according to claim 19, wherein said supporting corset further comprises a glue bead preferably extending in a longitudinal direction of said hose member and connecting each two directly adjacent hose members.

22. An endoscope shaft according to claim 2, further comprising a means for reducing a swelling of each respective hose member transversely to a longitudinal direction thereof, wherein said means for reducing said swelling further comprises a supporting corset arranged on an outside of said hose member, and wherein said supporting corset further comprises a plurality of collars or rings spaced apart in the longitudinal direction of said endoscope shaft, said collars or rings being placed into said grooves of said bellows aligned towards each other perpendicular to a central axis of said end portion.

23. An endoscope shaft according to claim 2, further comprising a means for reducing a swelling of each respective hose member transversely to a longitudinal direction thereof.

24. An endoscope shaft according to claim 23, wherein said means for reducing a swelling further comprises a supporting corset arranged on an outside of said hose member.

25. An endoscope shaft according to claim 24, wherein said supporting corset further comprises a helical spring which is placed into said grooves of said bellows aligned to form a helical shape.

26. An endoscope shaft according to claim 24, wherein said supporting corset further comprises a reinforced hose envelope.

* * * * *